(12) United States Patent
Kirchner

(10) Patent No.: US 11,737,863 B2
(45) Date of Patent: Aug. 29, 2023

(54) INTRAOCULAR LENS WITH A SPREADABLE HAPTIC

(71) Applicant: Carl Zeiss Meditec AG, Jena (DE)

(72) Inventor: Friedrich Kirchner, Berlin (DE)

(73) Assignee: CARL ZEISS MEDITEC AG, Jena (DE)

( * ) Notice: Subject to any disclaimer, the term of this patent is extended or adjusted under 35 U.S.C. 154(b) by 107 days.

(21) Appl. No.: 17/631,554

(22) PCT Filed: Jul. 8, 2020

(86) PCT No.: PCT/EP2020/069253
§ 371 (c)(1),
(2) Date: Jan. 31, 2022

(87) PCT Pub. No.: WO2021/018533
PCT Pub. Date: Feb. 4, 2021

(65) Prior Publication Data
US 2022/0313421 A1 Oct. 6, 2022

(30) Foreign Application Priority Data
Jul. 31, 2019 (DE) ...................... 10 2019 211 435.0

(51) Int. Cl.
*A61F 2/16* (2006.01)
(52) U.S. Cl.
CPC .......... *A61F 2/1613* (2013.01); *A61F 2/1648* (2013.01); *A61F 2002/1681* (2013.01); (Continued)
(58) Field of Classification Search
CPC .................. A61F 2/1613; A61F 2/1648; A61F 2002/1681; A61F 2002/1689; A61F 2002/16903
See application file for complete search history.

(56) References Cited

U.S. PATENT DOCUMENTS 3,994,027 A 11/1976 Jensen et al.
2004/0215340 A1 10/2004 Messner et al.

FOREIGN PATENT DOCUMENTS

| DE | 10310961 B4 | 12/2006 |
| DE | 102007057122 A1 | 6/2008 |
| WO | WO-2003/015668 A1 | 2/2003 |

OTHER PUBLICATIONS

Written Opinion of the International Searching Authority for PCT/EP2020/069253 (ISA/CN) dated Oct. 26, 2020 (5 pages).
(Continued)

*Primary Examiner* — William H Matthews
(74) *Attorney, Agent, or Firm* — Alston & Bird LLP

(57) ABSTRACT

Provided is an intraocular lens having an optical body and having at least one haptic element coupled to the optical body, wherein the at least one haptic element has a first haptic component and at least a second haptic component formed adjacent thereto, which is movable elastically relative to the first haptic component, and having a principal optical axis that penetrates through a front side and a reverse side of the optical body, wherein the haptic element, measured in the direction of the principal optical axis, has a maximum of a first height, wherein the second haptic component is displaceable relative to the first haptic component from a non-spread position to a spread position in such a way that the haptic element, measured in the direction of the principal optical axis, attains a maximum of a second height which is greater than the first height, and, in the spread position, the second haptic component can be locked in place relative to the first haptic component, wherein the first haptic component has at least a first spreading element, and the second haptic component has at least a second spreading element, wherein the first spreading element and the second spreading element, viewed in circumferential direction around the principal optical axis, at least in the (Continued)

Figure 1:
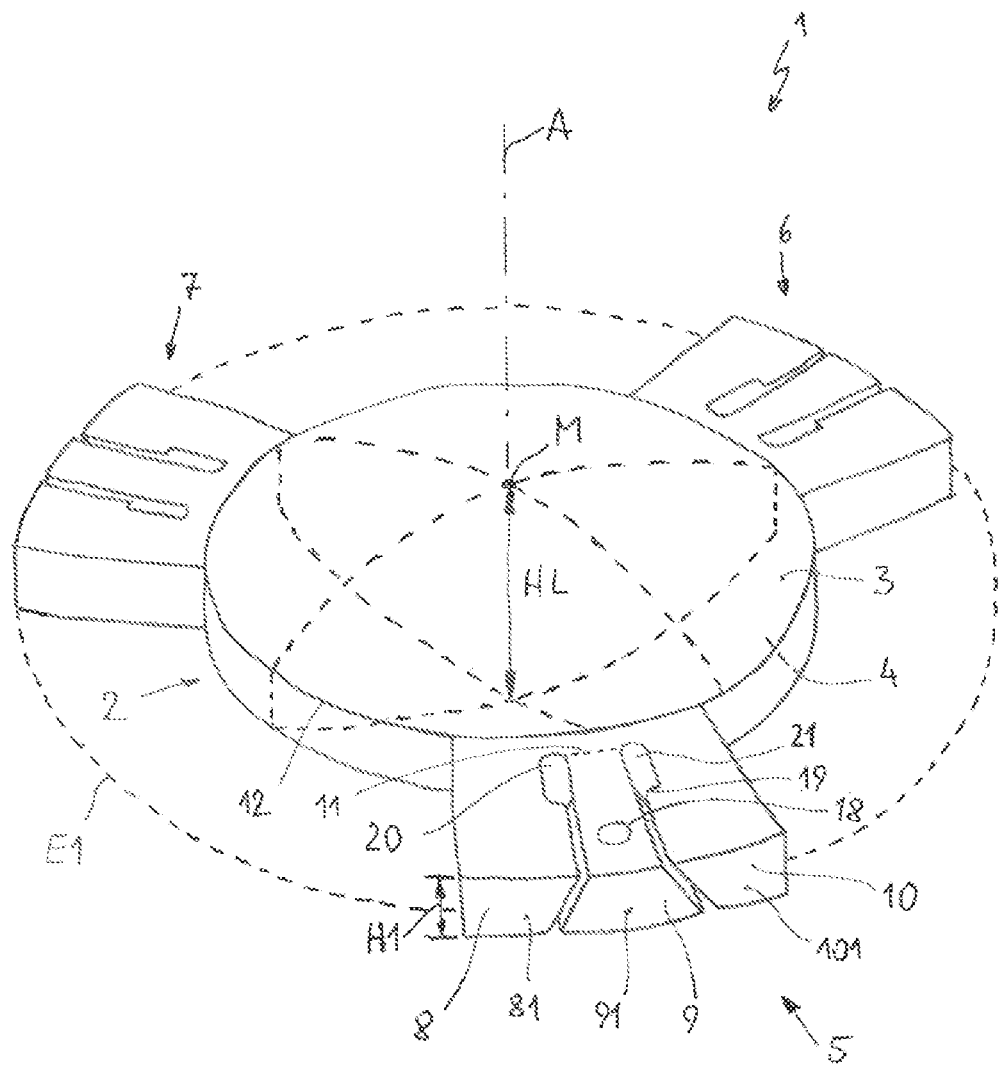

spread position, are in a mutually overlapping arrangement and directly adjacent to one another at least in some regions.

20 Claims, 10 Drawing Sheets

(52) U.S. Cl.
CPC ............... *A61F 2002/1689* (2013.01); *A61F 2002/16901* (2015.04); *A61F 2002/16903* (2015.04)

(56) References Cited

OTHER PUBLICATIONS

German Examination Report for German Patent Application No. 10 2019 211 435.0, dated May 7, 2020, (18 pages), German Patent and Trademark Office, Munich, Germany.
International Search Report and Written Opinion for International Application No. PCT/EP2020/069253, dated Oct. 26, 2020 (11 pages), European Patent Office, Rijswijk, Netherlands.

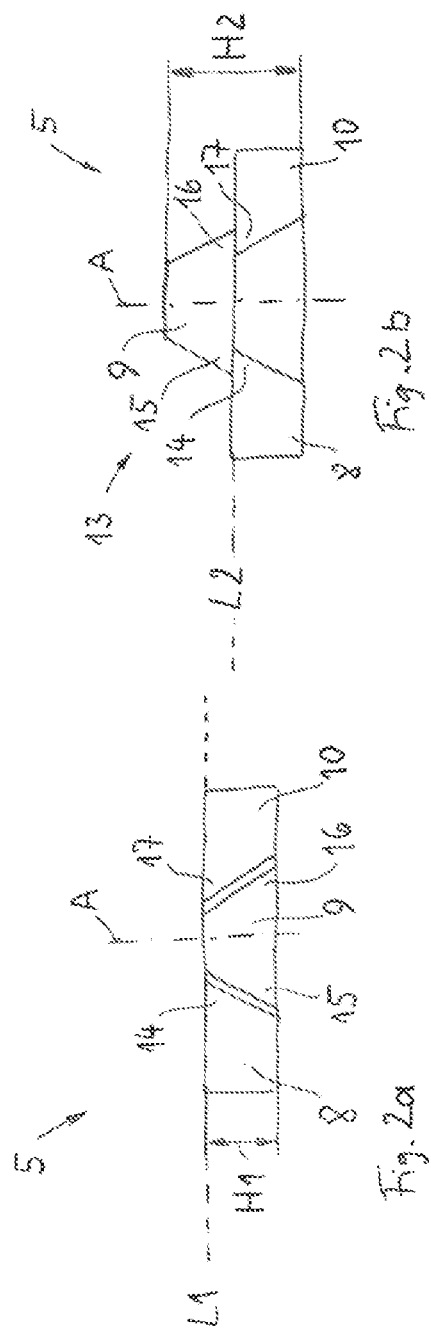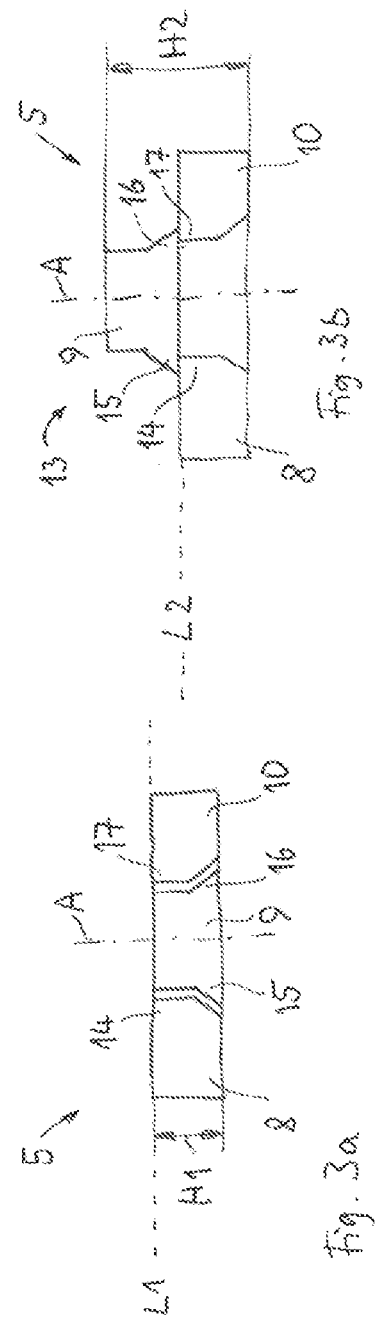

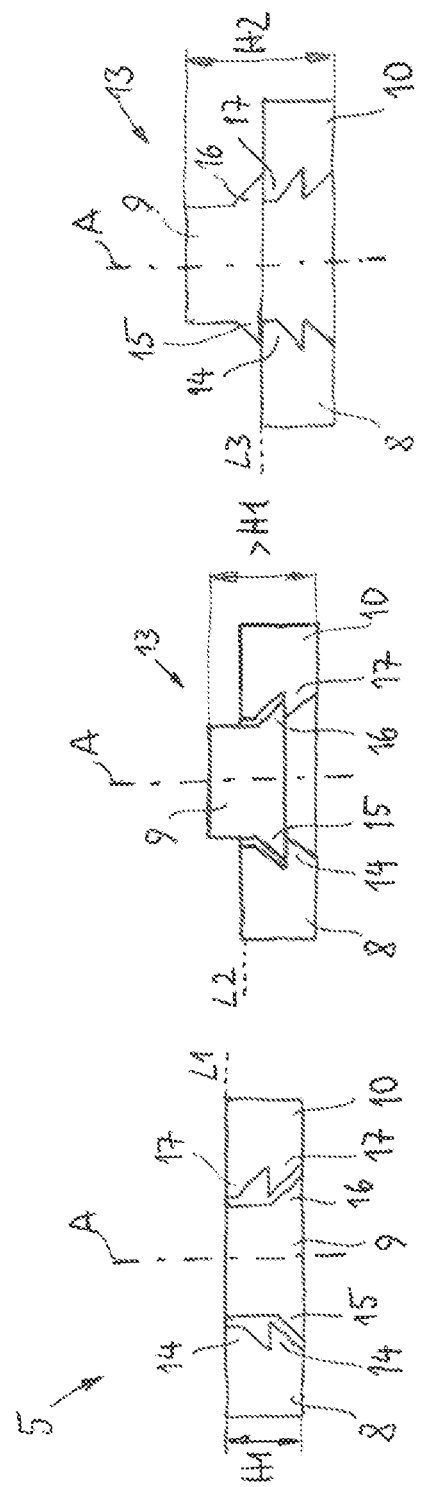

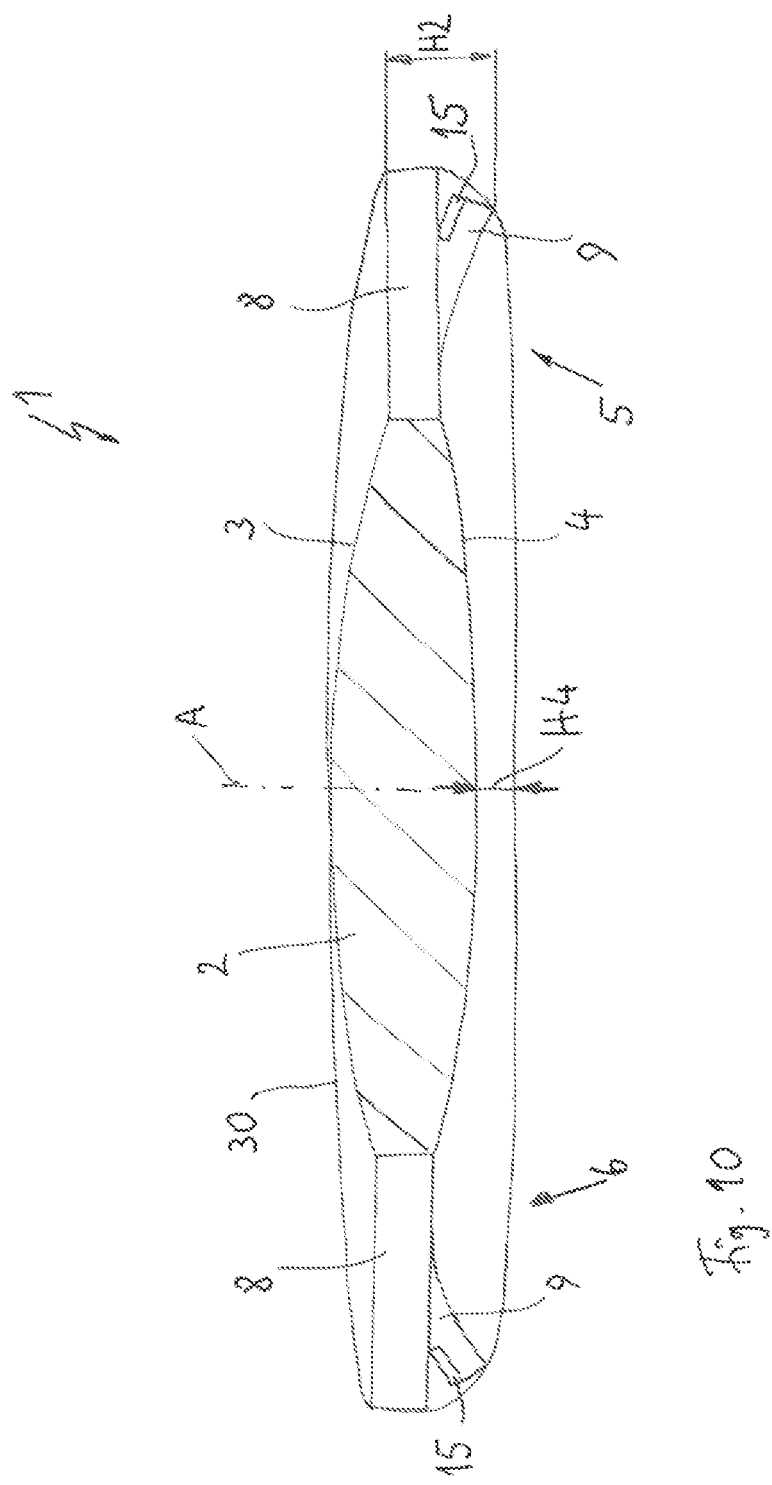

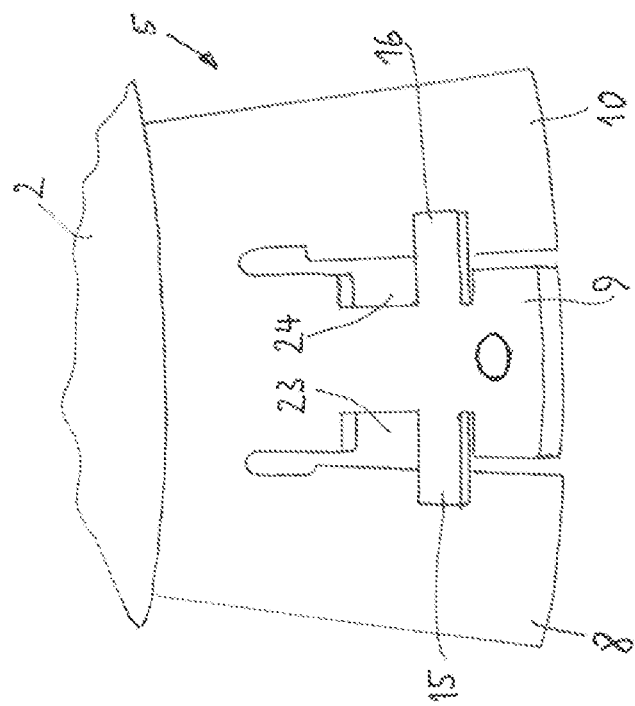
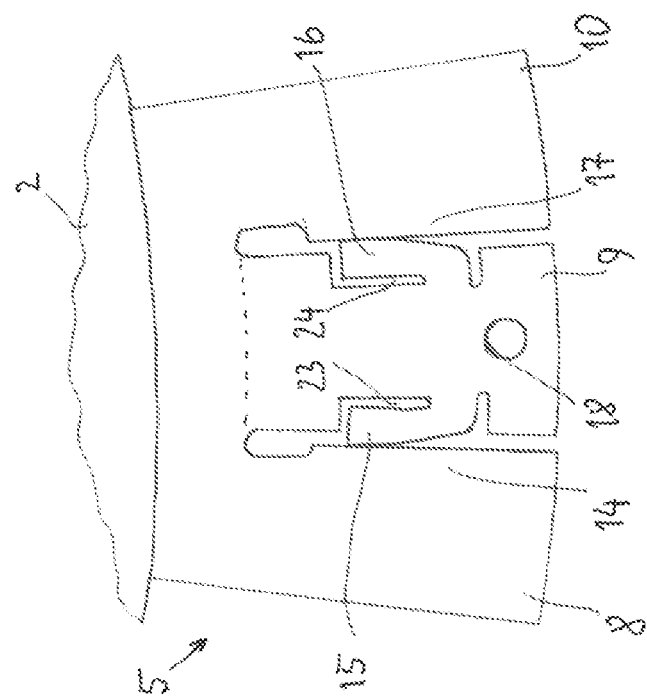

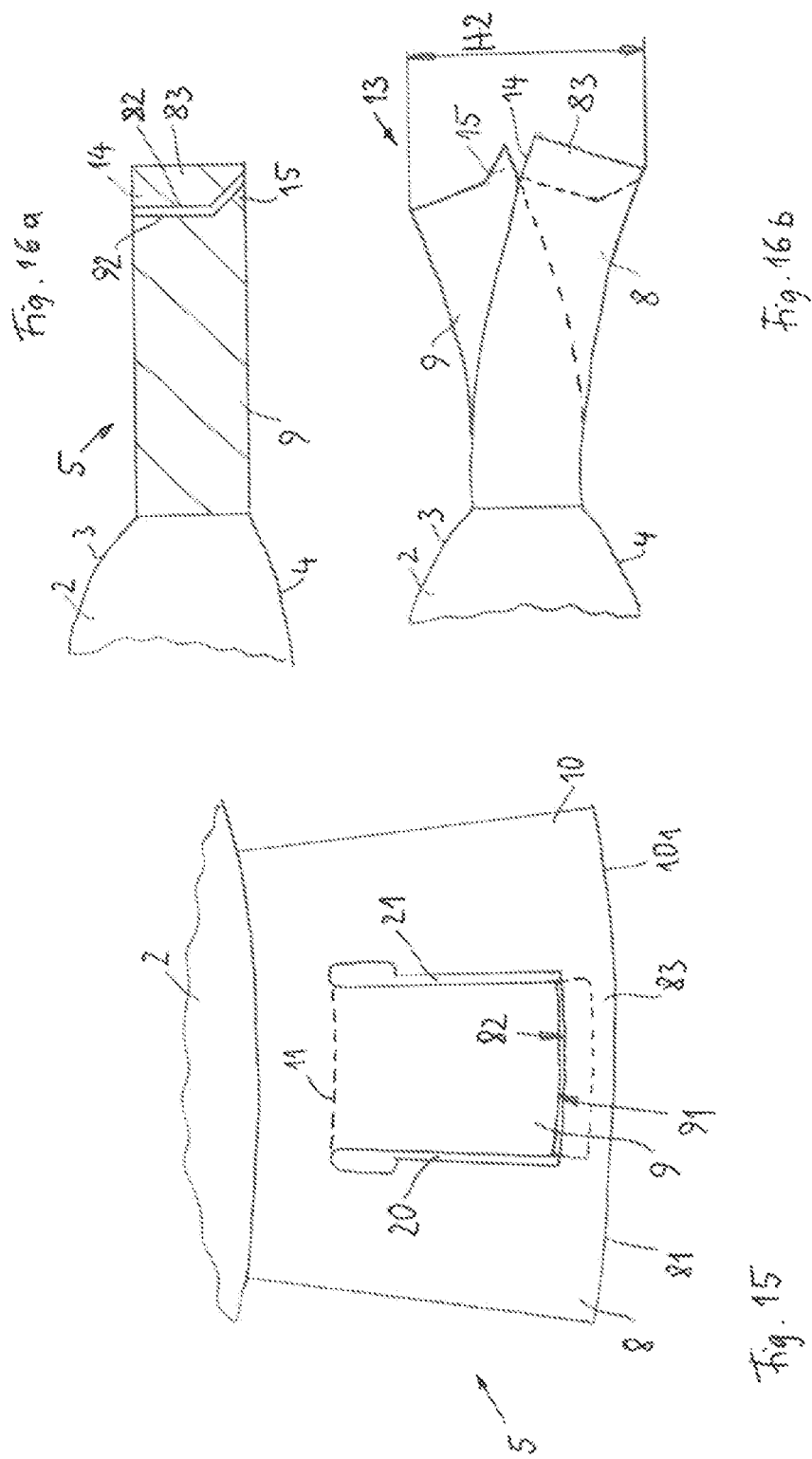

INTRAOCULAR LENS WITH A SPREADABLE HAPTIC

CROSS-REFERENCE TO RELATED APPLICATIONS

The present application is a national phase entry of International Application No. PCT/EP2020/069253, filed Jul. 8, 2020, which claims priority to German Patent Application No. 10 2019 211 435.0, filed Jul. 31, 2019, which are incorporated herein by reference in their entirety.

TECHNICAL FIELD

The invention relates to an intraocular lens having an optical body and having at least one haptic element coupled to the optical body. The intraocular lens has a principal optical axis that penetrates through a front side and a reverse side of the optical body. This at least one haptic element has a first haptic component, and at least a second haptic component formed adjacent thereto. The second haptic component is movable elastically relative to the first haptic component.

PRIOR ART

Intraocular lenses are known in various configurations. Typically, intraocular lenses have at least two separate haptic elements formed opposite one another in circumferential direction around the principal optical axis and coupled to the optical body. It is also possible for more than two such separate haptic elements to be formed, for example three haptic elements.

Intraocular lenses may be implanted in place of a natural lens of the eye at different defined positions within the eye. It is thus envisaged in this context that specific intraocular lenses are implanted in an anterior chamber of the eye. For example, such anterior chamber lenses may be fixed in the anterior iridocorneal angle.

There are also known intraocular lenses that are referred to as iris clip lenses. Such intraocular lenses are secured to the pupil. In particular, they are clipped to the pupil opening. Such an intraocular lens is known, for example, from DE 10 2007 057 122 A1. The intraocular lens therein, with this specific implantation site in the eye, has two opposite haptic elements. Each of these haptic elements has two C-shaped haptic arms. Mutually facing ends of these haptic arms, viewed in a plane at right angles to the principal optical axis of this intraocular lens, are arranged so as to face one another, but arranged contactlessly and without overlap. By means of haptic arms formed in this way, the gap formed in circumferential direction around the principal optical axis between the ends of the haptic arms can be used to clip onto the iris. However, such lenses are not intended for and not suitable for implantation in a capsular bag of an eye.

In this regard, there are further known specific intraocular lenses that can be referred to as posterior chamber lenses and can be implanted into a capsular bag of the eye.

DE 103 10 961 B4 discloses an intraocular lens which is a posterior chamber lens. In this posterior chamber lens, two separate haptic elements are formed radially adjoining the optical body in opposite regions of the optical body. Both the respective haptic elements are formed with two haptic components. The two haptic components of a haptic element are movable relative to one another. For this purpose, at a defined connection site between the haptic elements connected to one another in one-piece form, a defined kink point is formed, for example in the form of an integral hinge. In this way, the radially outer haptic component of this haptic element can be kinked or pivoted relative to the first haptic component that directly adjoins the optical body. This pivoting motion is possible only in the plane at right angles to the optical axis. This is intended to reduce the radial width of the overall intraocular lens in order to be able to avoid irritation in the interior of the capsular bag resulting from these haptic elements.

Furthermore, U.S. Pat. No. 3,994,027 A describes an intraocular lens having two haptic elements.

After implantation of an intraocular lens, an improvement in sight occurs, but this is subject to a distinct decline again within 5 years after the operation in about 45% of the more than 60-year-old patients. The cause is residual lens epithelial cells on an inner face of the capsular bag that remain after a cataract operation. As a result of proliferation, migration, epithelial-mesenchymal transition (EMT), variations in collagen and regeneration of lens fibers from lens epithelial cells, there is increasing opacification of the rear capsular bag wall, also called "aftercataract" or "posterior capsule pacification" or "PCO". Patients perceive such opacification as being very troublesome.

SUMMARY OF THE INVENTION

It is an object of the present invention to provide an intraocular lens with which the likelihood or intensity of an aftercataract can be reduced.

This object is achieved by means of an artificial intraocular lens according to the features of the independent claim.

One aspect of the invention relates to an intraocular lens having an optical body and having at least one haptic element coupled to the optical body. The intraocular lens has a principal optical axis that penetrates through a front side and a reverse side of the optical body. The haptic element has a first haptic component and at least a second haptic component formed adjacent thereto, which is elastically movable relative to the first haptic component. The haptic element has a maximum of a first height in the direction of the principal optical axis. This means that this first height must not cover the entire extent of the haptic element in radial direction. Instead, it is sufficient when such a height exists at least at one point along the extent in radial direction. The second haptic component is movable relative to the first haptic component from a non-spread position to a spread position in such a way that the haptic element, measured in the direction of the principal optical axis, has a maximum of a second height which is greater than the first height. The first height is therefore less than the second height at every point in the haptic element. The second height may therefore exist only in the spread position of the two haptic components. Moreover, in the spread position, the second haptic component can be locked in place relative to the first haptic component.

According to the invention, the first haptic element has at least one first spreading element, and the second haptic element has at least one second spreading element. These two spreading elements are in a directly adjacent arrangement in the non-spread position of the haptic components. They may thus also be positioned in contact with one another in the non-spread position.

According to the invention, the first spreading element and the second spreading element, at least in the spread position, are in a mutually overlapping arrangement, viewed in circumferential direction around the principal optical axis.

In this spread position, they are arranged directly adjacent to one another at least in some regions.

Such a configuration of the intraocular lens enables achievement of at least two defined positions by means of the first haptic component and the second haptic component. More particularly, the spread position is intended to achieve a smaller area of contact of a capsular bag wall, especially of the posterior capsule bag wall, with a reverse side of the optical body in the implanted state of the intraocular lens in a capsular bag. It is thus possible for aqueous humor to get between this reverse side of the optical body and the posterior capsular bag wall, for example, such that some of the troublesome cells, rather than remaining there, can be washed away. This is advantageous since opacification of the posterior capsular bag wall and hence formation of aftercataract can at least be reduced compared to conventional capsular bag-implanted intraocular lenses.

By virtue of the first spreading element and the second spreading element, in the spread position, being in an overlapping arrangement viewed in circumferential direction around the principal optical axis and being arranged directly adjacent to one another at least in some regions, the discrete spread position in which the two spreading elements and hence also the haptic components are adjusted with respect to one another in the direction of the principal optical axis and the haptic components are spread out in this way is achieved in a particularly advantageous manner. More particularly, this also achieves corresponding mechanical stability with regard to the maintenance of the spread position.

It is pointed out that, in this document, the anterior capsular bag wall is oriented toward the cornea, whereas the posterior capsular bag wall is oriented toward the retina.

In the spread position, the first haptic component and the second haptic component form a spread connection. Since the first haptic component and the second haptic component can be locked in place in the spread position, this spread position can be maintained for a prolonged period of time. An automatic return of the two haptic components from the spread position to the non-spread position is prevented. More particularly, this spread connection is designed appropriately for the purpose.

A spread connection is understood to mean a connection in which at least one component to be deformed is deformed and joined and remains in its final position with low stress. At least in one subregion, this component is under permanent deformation when it is in the spread position.

In particular, the intraocular lens is in one-piece form.

In an advantageous execution, the second height is at least such that a maximum height of the optical body measured in vertical direction or in the direction of the principal optical axis is less than this second height. This second height is thus greater than a maximum thickness of the optical body measured in the direction of the principal optical axis. It may be the case that the maximum thickness or height of the optical body is in the geometric center of the optical body. In this case, the maximum thickness of the optical body may be referred to as center thickness.

This working example also ensures that there is no contact between one side of the optical body of the intraocular lens and a wall of the capsular bag under tension. More particularly, direct contact between the reverse side of the optical body and the posterior capsular bag wall is thus avoided. When the spread position has the effect that the entire posterior capsular bag wall, after implantation of the intraocular lens, is at a distance from the reverse side of the optical body, even better flushing of the optical body with aqueous humor is possible, such that it is possible to further reduce the probability of formation of an aftercataract.

In an advantageous execution, the at least two haptic components of the at least one haptic element are arranged in the non-spread position of the haptic components and hence in a default position of the haptic components in a common plane oriented at right angles to the principal optical axis. More particularly, these haptic components in this non-spread position are then not opposite one another either in one direction of the principal optical axis or in the other direction of the principal optical axis.

In the spread position, at least one of the two haptic components is positioned such that it projects out of this common plane. Preferably, in the spread position, both the first haptic component and the second haptic component project out of the plane in which the two haptic components are present in the non-spread state.

Preferably, the first height is considered at the thickest point in the haptic element in the non-spread position, and the second height at the thickest point in the haptic element in the spread position.

More particularly, the at least two haptic components that are movable relative to one another in the at least one haptic element are arranged adjacent to one another around the principal optical axis, i.e. in azimuthal direction, preferably arranged directly adjacent to one another. In one embodiment, they may be in contact both in the non-spread position and in the at least one spread position. The at least two haptic components may alternatively be arranged at a distance from one another in the non-spread position.

It may be the case that the artificial intraocular lens has at least one second haptic element. More particularly, the second haptic element likewise has at least two haptic components as elucidated above for the first haptic element. It may also be the case that the artificial intraocular lens has at least three such separate haptic elements that are spaced apart from one another and equidistantly from one another in circumferential direction around the principal optical axis. This possible third haptic element too may advantageously have at least two haptic components that are movable elastically with respect to one another. More particularly, this mobility is in the direction of the principal optical axis.

In an advantageous execution, in the spread position of the two haptic components of this at least one haptic element, these haptic components directly adjoin one another at at least one point and are spread with respect to one another. This achieves a reliable and stable spread connection. The haptic components preferably lie against one another under stress.

It is preferably the case that at least one spreading element is designed for configuration of such an azimuthal overlap with an undercut.

It is preferably the case that at least one spreading element, preferably all spreading elements, are elastic. The at least one spreading element preferably has a Shore A hardness in the range from 60 to 100 to ISO 7619-1. This enables displacement of one haptic component having such a spreading element from the non-spread position to the spread position with relatively low expenditure of force. Plastic deformation at the bending line of such a haptic component can thus be avoided.

In an advantageous embodiment, it may be the case the first spreading element and the second spreading element, at least in the spread position, are in a mutually overlapping arrangement, viewed in radial direction relative to the principal optical axis. More particularly, they may also be in a directly adjoining arrangement at least in some regions.

Such a configuration may form an alternative to the above-mentioned azimuthal overlap or be formed in combination therewith. For example, depending on the geometry of a haptic element and/or the size of the intraocular lens and/or the configuration of a capsular bag, it is then possible to provide a spread connection which is individually suitable in this regard. More particularly, in this connection, it is possible to provide different intraocular lenses formed with different configurations of spread connections.

In an advantageous execution, the at least two spreading elements are arranged on the at least two haptic components such that, in the non-spread position of the haptic components, they do not protrude beyond the two haptic components either in the direction of the principal optical axis or in circumferential direction around the principal optical axis. As a result, it is possible to avoid an increase in geometric size and/or unwanted complexity of shape of the haptic element. On the one hand, this enables the adjustment of the spread position in a simple manner.

In an advantageous embodiment, the spreading elements are of wedge-shaped cross section. This means that the spreading elements may be moved past one another from the non-spread position to the spread position with low friction force in the direction of the principal optical axis. It is thus possible to avoid jerky or abrupt transitions.

It may be the case that the two spreading elements of the two haptic components are formed on mutually facing surface regions of these two haptic components. More particularly, these may in one-piece form therewith. It may be the case that at least one spreading element takes the form of a one-piece, coherent and hence uninterrupted element. For example, this may take the form of a bar or rail. A spreading element may be in linear form. A spreading element may be formed with its longitudinal axis running at right angles to the principal optical axis. In this connection, it extends in a linear manner and radially relative to the principal optical axis. It may also be the case that a spreading element, viewed in radial direction, is in an inclined arrangement relative to the principal optical axis. More particularly, this relates to a contact surface provided in the spread position for it to directly adjoin the other spreading element.

It is likewise possible for one of the two spreading elements to be formed from at least two separate spreading component elements. These may be arranged spaced apart from one another in radial direction and/or in the direction of the principal optical axis.

It may also be the case that at least one spreading element takes the form of a pin or peg. It may be the case that a spreading element, in the non-spread position of the haptic components relative to one another, is disposed in a default position relative to the haptic component, and, in a spread position, is disposed in a different hold position. In such a configuration, it is thus the case that a spreading element is in one-piece form on the haptic component and is movable relative to this haptic component. For example, a spreading element may take the form of an elastic spring element. This elastic spring element may be a sprung peg or a sprung pin. More particularly, a spreading element in such a form, in the default position, may be within a cutout in the corresponding haptic component under prestress. By virtue of the adjacent other haptic component adjoining this spreading element, this default position of the spreading element is maintained. If the haptic component is then moved relative to the other haptic component and the hold function for the prestressed spreading element is released, the spreading element moves automatically from its default position to the hold position and overlaps the other haptic component of the haptic element in azimuthal direction and/or radial direction. The spread position is then formed and is held by the spreading elements themselves.

In alternative executions, it may be the case that, even when a spreading element is formed from one or more spreading component elements, these spreading component elements extend to a correspondingly equal degree both in the default position and in the hold position and extend in the same direction.

If the spreading elements take the form of pegs or pins in such a configuration, it is possible for the complementary second spreading component elements of the second spreading element to take the form of depressions or grooves or channels into which the first spreading component elements mesh. These depressions or channels are closed by a wall at least at one particular end. As a result, when a first spreading component element is guided away from or out of a second spreading component element, the spread position is established, and the overlap then created between the two spreading component elements prevents the haptic components from returning from the spread position to the non-spread position.

Specifically when a spreading element has at least two spreading component elements, it is possible for at least two different spread positions to be implemented. Each of these individual discrete spread positions may then be maintained individually depending on the setting of the spread connection, and the respective spread position may be blocked.

In an advantageous execution, at least one coupling elevation or coupling depression is formed on a top face of at least one haptic component. This coupling elevation or coupling depression is set up for engagement of an adjustment tool for establishment of a specific spread position of the haptic components relative to one another. As a result, it is possible in a simple manner for medical personnel to define and quickly establish the spread position or one of possible spread positions. Such a coupling elevation may, for example, be a clip that can be hooked onto a corresponding hook-shaped adjustment tool. As a result, it is then possible to displace the haptic component correspondingly with respect to the at least one further haptic component of the at least one haptic element in the direction of the principal optical axis, i.e. vertically upward or downward, or to displace it radially in the direction of the principal optical axis, in order then to establish the spread position in a defined manner. Displacement in the direction toward the principal optical axis can be effected in such a way that a haptic component is compressed or squashed in terms of its longitudinal extent. In order to avoid unwanted protrusions on the haptic components, it is advantageously possible to provide a coupling depression. This may be, for example, a blind hole or else a passage hole. Such a coupling depression may also have an undercut. By virtue of this configuration in the form of an undercut, which can also be referred to as a cutout, it is again possible to achieve specific engagement with an adjustment tool. As a result, it is less likely that an adjustment tool will slide off the haptic component in the establishment of a spread position.

It may be the case that, in the spread position of the at least two haptic components, the second height is formed at the distal end, i.e. at the radially outer end, of the two haptic components. This may be the case when the at least two haptic components of the haptic element, viewed in radial direction to the optical axis, are separated at their free, radially outer ends.

In an alternative execution, it may be the case that the at least two haptic components of a haptic element in question, in the spread position, also directly adjoin one another at these radially outer ends.

It may also be the case that, in one working example, the at least two haptic components are designed as radially aligned bars oriented parallel to one another. More particularly, the two such haptic components are oriented parallel to one another. They are especially in linear form. It may be the case that the two haptic components are connected directly to one another over part of their overall radial length. More particularly, this part of the length may be directed radially outward proceeding from an end that opens onto the optical body.

This means that a bending edge about which that haptic component which is adjusted relative to the at least one other haptic component in the displacement into the spread position is spaced apart from the optical body and is formed in the haptic element itself. Unwanted impairments of the optical body in the case of such bending and maintenance of this bending in the spread position can thus be avoided.

In an advantageous execution, it may be the case that one haptic component takes the form of a strip or bar oriented radially. The at least one further haptic component, viewed in a plane at right angles to the principal optical axis, may be formed so as to surround this haptic component in the manner of a frame. For example, this other haptic component may be U-shaped and in one-piece form. The various working examples set out above may also be formed in the case of such a configuration of a haptic element.

More particularly, the intraocular lens takes the form of an intraocular lens implanted in a capsular bag. It may also be referred to as a capsular bag-implanted intraocular lens. More particularly, it is a posterior chamber lens for implantation into a capsular bag of an eye. This means that the intraocular lens is intended, especially solely, for implantation into a capsular bag of an eye.

In an advantageous execution, a haptic element has three haptic components. These haptic components may be formed so as to be adjacent and directly adjoining one another in circumferential direction around the principal optical axis. Especially in the case of such a configuration, the middle haptic component in azimuthal direction, in the establishment of the at least one spread position, is adjusted relative to the two other haptic components, and each, especially viewed azimuthally, has opposite first spreading elements that adjoin second spreading elements formed integrally in the two other haptic components and is spread in this way.

Further features of the invention are apparent from the claims, the figures and the description of the figures. The features and combinations of features mentioned in the description above and the features and combinations of features mentioned in the description of the figures below and/or shown in the figures alone may be used not only in the respectively specified combination but also in other combinations, without departing from the scope of the invention. The invention shall thus also be considered to include and disclose embodiments of the invention that are not shown and elucidated explicitly in the figures, but result and can be created from separate combinations of features from the details elucidated. Disclosure shall also be considered to extend to embodiments and combinations of features that thus do not have all the features of an independent claim as originally worded. Disclosure shall additionally be considered to extend to embodiments and feature combinations, in particular by virtue of the embodiments explained above, which go beyond or depart from the feature combinations set out in the dependency references of the claims.

The specific values indicated in this document for parameters and data relating to ratios of parameters or parameter values for the definition of working examples of the eye lens should be considered to be encompassed by the scope of the invention even within the scope of deviations, for example on account of measurement errors, system faults, DIN tolerances, etc., which means that this shall also be understood to include elucidations relating to substantially corresponding values and indications.

Figure 5:
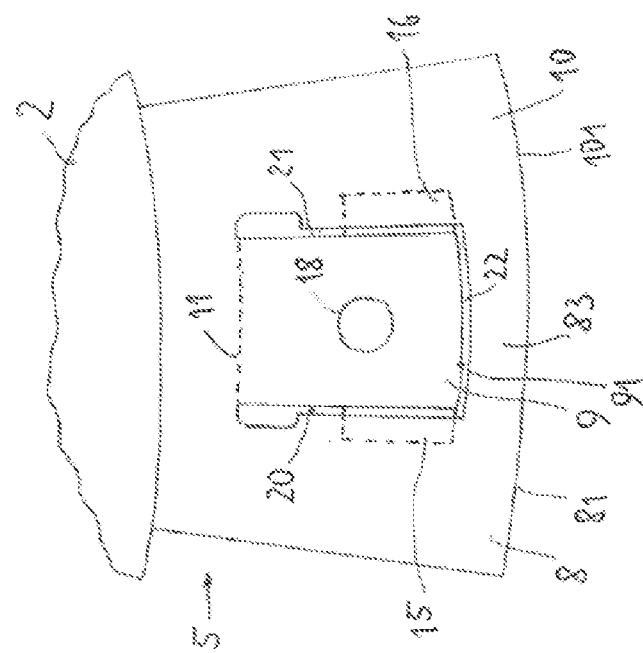
Figure 6:
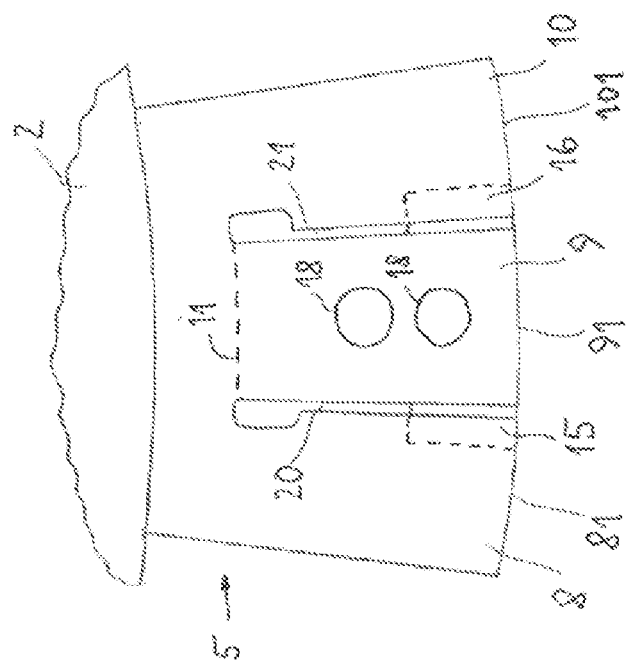
Figure 8:
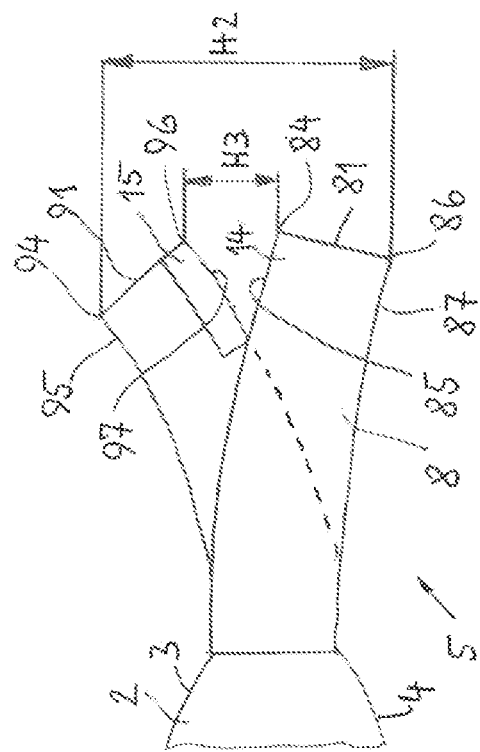
Figure 7:
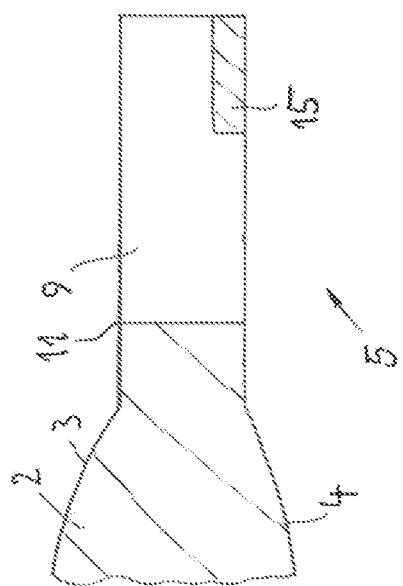
Figure 9:
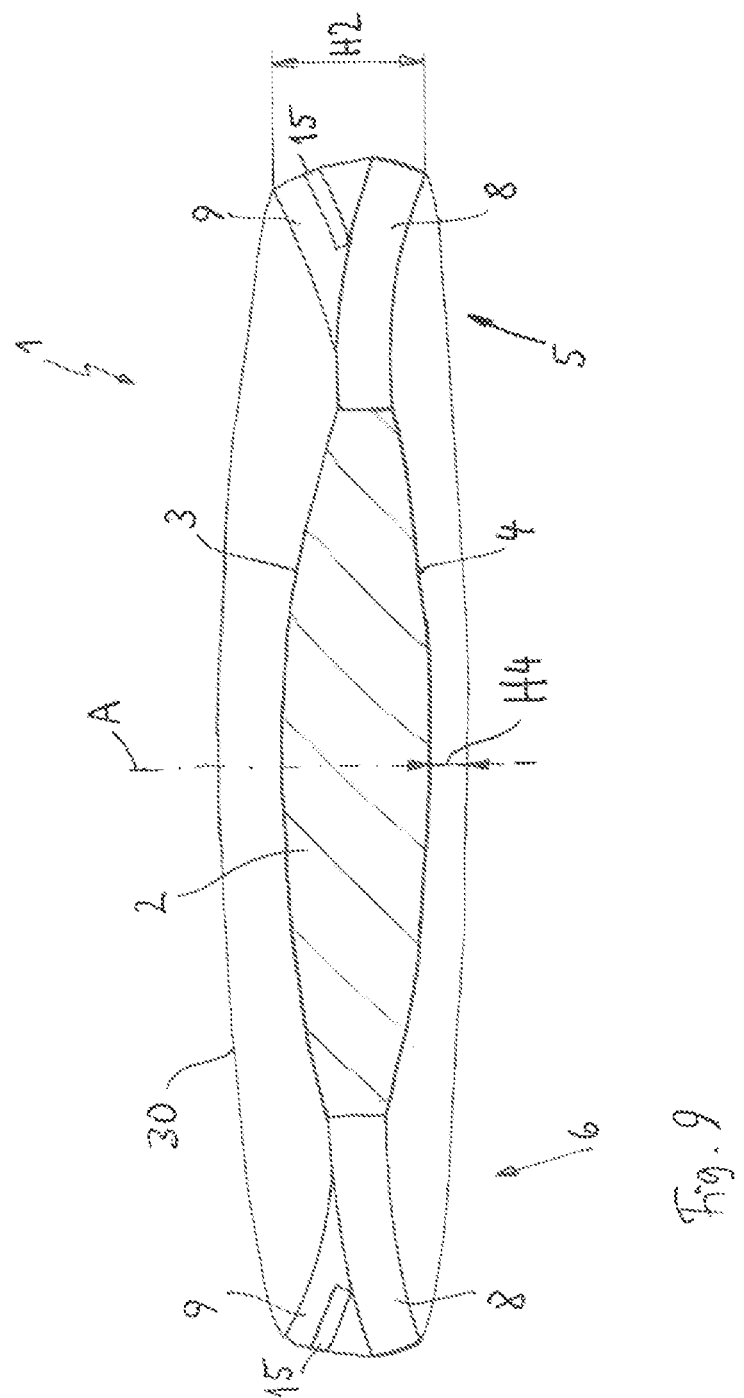
Figure 12:
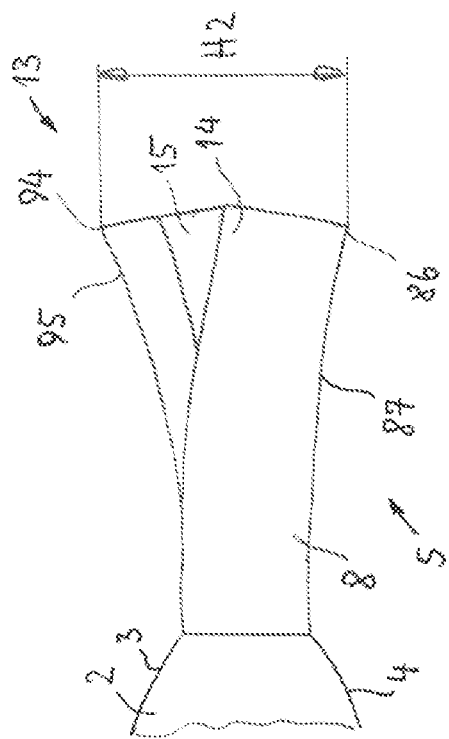
Figure 11:
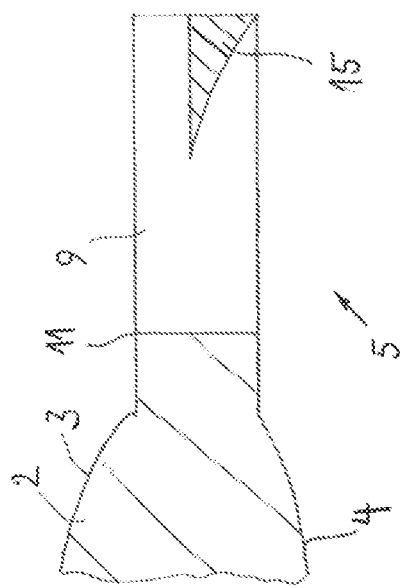

Working examples of the invention are explained in greater detail below with reference to schematic drawings. The figures show:

FIG. 1 a schematic perspective diagram of a working example of an artificial intraocular lens;

FIG. 2a a front view of a haptic element of an intraocular lens according to FIG. 1 in a non-spread position of haptic components of this haptic element;

FIG. 2b a diagram according to FIG. 2a, showing a spread position of the haptic components relative to one another;

FIG. 3a a front view of a haptic element of an intraocular lens in a further embodiment, in a non-spread position of haptic components of this haptic element;

FIG. 3b the diagram of the haptic components according to FIG. 3a, except that FIG. 3b shows a spread position of the haptic components;

FIG. 4a a front view of a haptic element of an intraocular lens in a further embodiment, in a non-spread position of haptic components of this haptic element;

FIG. 4b a diagram of the haptic components according to FIG. 4a, except that FIG. 4b shows a first spread position of the haptic components;

FIG. 4c a diagram of the haptic components according to FIG. 4a and FIG. 4b, except that FIG. 4c shows a second spread position of the haptic components;

FIG. 5 a top view of a haptic element of an intraocular lens in a further embodiment;

FIG. 6 a top view of a haptic element of an intraocular lens in a further embodiment;

FIG. 7 a section diagram of the intraocular lens with a haptic element according to FIG. 5;

FIG. 8 a side view of part of the intraocular lens according to FIG. 7, in which the haptic components are shown in a spread position;

FIG. 9 a cross-sectional view through a capsular bag with an implanted intraocular lens showing a haptic element as shown in FIG. 8;

FIG. 10 a cross-sectional view through a capsular bag with an implanted intraocular lens showing a haptic element as shown in FIG. 6;

FIG. 11 a section diagram of an intraocular lens with a haptic element in a further embodiment;

FIG. 12 a side view of the intraocular lens according to FIG. 11, in which the haptic components are shown in a spread position;

FIG. 13 a schematic diagram of a further working example of an intraocular lens with a haptic element in a top view, with the haptic components in a non-spread position;

FIG. 14 a schematic diagram of a further working example of an intraocular lens with a haptic element in a top view, in which the haptic components are in a spread position;

FIG. 15 a diagram of a further working example of an intraocular lens with a haptic element in a top view;

FIG. 16a a section diagram through a haptic element of an intraocular lens according to FIG. 15, wherein the haptic components are in a non-spread position;

FIG. 16b a side view of a haptic element of an intraocular lens according to FIG. 15, wherein the haptic components are in a spread position;

PREFERRED WORKING EXAMPLES OF THE INVENTION

In the figures, identical or functionally equivalent elements are given the same reference symbols.

FIG. 1 shows a perspective view of a working example of an artificial intraocular lens 1. This intraocular lens 1 is a posterior chamber lens for implantation into a capsular bag of an eye. It may therefore also be referred to as a capsular bag-implanted intraocular lens. The intraocular lens 1 has an optical body 2 in the form of a lens. It is designed to create a defined optical imaging characteristic of the intraocular lens 1. The intraocular lens 1 has an optical axis or principal optical axis A that penetrates through a front side 3 of the optical body 2 and a reverse side 4 of the optical body 2. In this embodiment, the optical axis A penetrates through the optical body 2 in its geometric center M. The intraocular lens 1 additionally has a first haptic element 5 which, viewed in radial direction from the principal optical axis A, adjoins the optical body 2. In the working example, the intraocular lens 1 additionally has a second haptic element 6 and a third haptic element 7. The three haptic elements 5 to 7 formed here by way of example are formed spaced apart from one another in circumferential direction around the principal optical axis A and especially arranged equidistantly from one another. The haptic elements 5 to 7 retain the intraocular lens 1 in a capsular bag.

In the working example, the haptic elements 5 to 7, of which there are at least two here, especially three, are preferably of identical design. The elucidation that follows with reference to the first haptic element 5 is therefore especially also applicable to the further haptic elements 6 and 7 that are provided here by way of example.

This haptic element 5 has a first haptic component 8 in the working example. In addition, it has a second haptic component 9. In the working example, it is envisaged that a third haptic component 10 additionally forms part of the first haptic element 5. The three haptic components 8 to 10 here are adjacent in azimuthal direction with respect to the principal optical axis A and in a directly adjoining arrangement. There is therefore an arrangement of an ensemble of multiple haptic components 8 to 10 that together forms the first haptic element 5. In the working example, the three haptic components 8 to 10 take the form of bars that extend in radial direction. They preferably have the same radial extent. More particularly, they are oriented outward in the manner of rays in the same direction with their longitudinal axes oriented radially relative to the principal optical axis A. In the non-spread position of the haptic components 8 to 10 with respect to one another, as shown in FIG. 1, these longitudinal axes are oriented in a common plane E1. This plane E1 is oriented at right angles to the principal optical axis A. The three haptic components 8 to 10 are separated from one another over at least a lengthwise portion of their radial extent and can thus move relative to one another. More particularly, at least the second haptic component 9 is elastically deformable. In the working example, it is envisaged for this purpose that the second haptic component 9 is movable relative to the two other haptic components 8 and 10, viewed in the direction of the principal optical axis A.

More particularly, it may be bent about a bending line 11 formed in the first haptic element 5 relative to the two other haptic components 8 to 10 in the direction of the principal optical axis A, i.e. in the vertical direction and especially vertically upward. This bending line 11 runs in circumferential direction around the principal optical axis A. In particular, this bending line 11 is radially spaced apart from an edge 12 of the optical body 2 and hence runs within the first haptic element 5.

The first haptic element 5 is designed such that the haptic components 8 to 10 are displaceable in the direction of the principal optical axis A, especially into at least two different positions. In the non-spread position shown in FIG. 1, the first haptic element has, or the haptic components 8 to 10 have, a maximum of a first height H1 measured in the direction of the principal optical axis A. This first height H1 should be understood such that it is measured at the position of the first haptic element 5 where the first haptic element 5 has its maximum height in this non-spread position. In the working example, it is envisaged that the first haptic element 5, in this non-spread position, is in plate form and has this first height H1 over its entire cross section.

According to the invention, the intraocular lens is formed such that the second haptic component is displaceable relative to the first haptic component 8 from a non-spread position to a spread position. In this at least one spread position, this first haptic element 5 has a second height H2. This second height H2, as is then elucidated hereinafter for FIG. 2b and further working examples, is greater than the first height H1. This second height H2 of the first haptic element 5 is again measured at that point in the first haptic element 5 where the first haptic element 5 attains a maximum height in the direction of the principal optical axis A measured in this spread position. This position may vary locally in a haptic element depending on the configuration of the haptic components 8 to 10 and/or the configuration of the spread connection 13. However, this is a secondary factor for functionality. It is essential that such a second height is formed in the spread position at at least one point in a haptic element. It is particularly advantageous when, in the case of an implanted intraocular lens 1, the second height H2 is greater than a maximum thickness, for example a center thickness HL, of the optical body 2. This makes it possible for an intraocular lens 1 implanted in a capsular bag not to touch the capsular bag wall with its optical body 2. Particularly the reverse side 4 of the optical body 2 of the intraocular lens 1 can thus be arranged spaced apart from a posterior capsular bag wall.

FIG. 2a shows a schematic diagram of a front view of the first haptic element 5. As is further apparent in the execution in FIG. 1, the haptic components 8 to 10 are separate from one another up to their distal ends 81, 91 and 101.

As is apparent in FIG. 2a, the haptic components 8 to 10 are arranged such that they overlap in a top view. In the working example shown, the first haptic component 8 has a first spreading element 14. It is formed in an integrated manner at the side wall of the first haptic component 8 that faces the second haptic component 9. As is apparent in FIG. 2a, in this execution, this first spreading element 14 has a wedge-shaped cross section. It especially extends over the entire height of the first haptic component 8. This height is measured in the direction of the principal optical axis A, i.e. in vertical direction. It is additionally apparent that the second haptic component 9 has a second spreading element 15. It is likewise formed with a wedge-shaped cross section. It especially likewise extends over the entire height of the second haptic component 9. It is especially formed in an integrated manner at a side wall of the second haptic component 9 that faces the first haptic component 8. The two spreading elements 14, 15 are thus formed so as to be complementary and, in the non-spread position shown in FIG. 2a, are arranged adjacent to one another, preferably directly adjoining one another.

Furthermore, in the working example shown, the second haptic component 9 has a further second spreading element 16. This is integrated in a side wall facing the third haptic component 10. This third haptic component 10 has a further first spreading element 17. This is integrated in a side wall facing the second haptic component 9. These further spreading elements 16 and 17 too are formed with a wedge-shaped cross section. They especially likewise extend over the entire height of the second haptic component 9 and the third haptic component 10. As is also apparent in the further second spreading element 16 and the further first spreading element 17, these overlap in the non-spread position shown in FIG. 2a when the first haptic component 5 is viewed in a top view. They face one another and are shaped so as to be complementary. They especially also adjoin one another. By virtue of the configuration shown in FIG. 2a, the azimuthal cross-sectional area of the second haptic component 9 is in trapezoidal form.

In FIG. 2a, the second haptic component 9 is in a non-spread position with respect to the first haptic component 8. The second haptic component 9 may then be displaced into a spread position in the direction of the principal optical axis A, i.e. vertically upward, relative to the first haptic component 8. In the embodiment shown in FIG. 2b, the second haptic component 9 is additionally in a spread position relative to the third haptic component 10. For this purpose, the second spreading elements 15 and 16 of the second haptic component 9 were displaced via the first spreading elements 14 and 17. As is apparent in FIG. 2b, the spreading elements 15 and 14 that are moved past one another directly abut one another. This is analogously applicable to the spreading elements 16 and 17. They likewise directly adjoin one another. The effect of the vertical overlap of the spreading elements 15 and 16 and of the spreading elements 16 and 17 is that the haptic components can persist in this spread position and the spread position can thus be retained or locked in place.

When the second haptic component 9 is displaced via the first haptic component 8 and the third haptic component 10, the second haptic component 9 presses downward with the second spreading element 15 onto the first spreading element 14 in the direction of the principal optical axis A. At the same time, the further second spreading element 16 presses onto the further first spreading element 17, likewise with exertion of a force downward in the direction of the principal optical axis A. This leads to a displacement of the first haptic component 8 and of the third haptic component 10 in the downward direction. In the non-spread state of the haptic element 5, the top side of the first haptic element 5 is disposed in a position L1 in the space; cf. FIG. 2a. In the spread position, this top side is displaced downward in the direction of the principal optical axis A and reaches position L2 in the space; cf. FIG. 2b.

In other words: The second haptic component 9 may be displaced from its rest position vertically upward into a braced position, i.e. in the direction of the principal optical axis A. Once it has overcome the height of the first and third haptic components 8, 10, it exerts a force directed vertically downward onto the first haptic component 8 and third haptic component 10. The second haptic component 9 remains under elastic stress in the position above the first haptic component 8 and third haptic component 10, while the first haptic component 8 and the third haptic component 10 are simultaneously pushed downward by the second haptic component 9. Since the first haptic component 8 and third haptic component 10, and also the second haptic component 9, on account of the spreading elements 14 to 17, do not return to the original rest position but are displaced into a respectively new plane in a sustained manner, this is a spread configuration. The first haptic component 8 and the third haptic component 10 therefore form a spread connection with the second haptic component 9.

This spread position is locked in place by the spreading elements 14 to 17 and does not return to the non-spread position of its own accord. In this spread position too, the spreading elements 14 and 15, and 16 and 17, overlap in azimuthal direction. The drawing in FIG. 2b includes the second height H2; in the working example, it is twice the first height H1.

For movement of the second haptic component 9, in an advantageous configuration, a coupling element may be provided. In the working example according to FIG. 1, this coupling element is enabled by a coupling depression 18 formed in the second haptic component 9. It is possible for an adjustment tool to mesh into this coupling depression 18, in order to bend this second haptic component 9 upward according to the diagram, such that the discrete spread position of the haptic components 8 to 10 relative to one another as shown in FIG. 2b can be established.

It may be the case that these spreading elements 14 to 17 take the form of linear rails. These may extend in radial direction in accordance with their wedge shape. They may extend at right angles to the principal optical axis A over their entire radial longitudinal extent. This means that a longitudinal axis of a spreading element 14 to 17 oriented in radial direction is oriented at right angles to the principal optical axis A. However, another possibility is an arrangement in which an inclination of such a longitudinal axis of a spreading element 14 to 17 to the principal optical axis A is formed.

It may be the case that a spreading element 14 to 17 extends essentially over the entire longitudinal extent of a haptic component 8 to 10. It is preferably the case that such a spreading element 14 to 17 extends only over part of the total length of a haptic component 8 to 10 measured in radial direction. What is envisaged in FIG. 1 in this working example is that the spreading elements 14 to 17 extend only over part of the length proceeding from the distal ends 81, 91 and 101 up to, for example, half or two thirds of the total radial length of the haptic components 8 to 10. For example, a radially inner end of the spreading elements 14 to 17 may be formed at the point 19 as shown in FIG. 1. In the working example, in this connection, it is then also possible for cutouts 20 and 21 to be formed between the haptic components 8 and 9, and 9 and 10. By virtue of these cutouts, the mobility of the second haptic component 9 in the case of bending around the bending line 11 can be improved, and it is then not blocked by spreading elements 14 to 17 that extend into it.

FIG. 3a shows, in a corresponding front view as in FIG. 2a, a further working example of an intraocular lens 1 with a first haptic element 5. By contrast with the diagram according to FIG. 2a, the second spreading elements 15 and 16 here do not extend over the entire height of the second haptic component 9. More particularly, at least subregions of the mutually facing side walls of the haptic components 8 and 9, and 9 and 10, are oriented vertically here. FIG. 3b, in a corresponding section diagram, again analogously to FIG. 2a, shows the spread position of the haptic components 8 to 10 relative to one another.

In each of the working examples shown in FIGS. 2a to 3b, just one spread position is possible.

FIG. 4a shows, in a front view corresponding to FIG. 2a and FIG. 3a, a working example in which the second haptic component 9 is displaceable relative to the first haptic component 8 into at least two discrete different spread positions. FIG. 4a shows the non-spread position of the haptic components 8 to 10 relative to one another. FIG. 4b shows a first spread position of the second haptic component 9 relative to the first haptic component 8. In this spread position, the two spreading element 15 and 16 of the second haptic component 9 are arranged so as to mesh into groove-like cutouts in the side walls of the lateral haptic components 8 and 9. In this way, the second haptic component 9 is again held and locked in place in this first spread position relative to the first haptic component 8. In this working example, the first haptic component 8 has two separate first spreading elements 14. This relates to an upper and a lower first spreading element 14. Two separate first spreading elements 17 are also formed correspondingly in the third haptic component 10. More particularly, these first spreading elements 14 are arranged one on top of another and hence stacked axially as viewed in the direction of the principal optical axis 8. The first spreading elements 17 are formed correspondingly in the third haptic component 10. Here too, the respective spreading elements 14, 15, 16 and 17 are in one-piece form with the respective haptic components 8, 9 and 10.

The diagram according to FIG. 4c shows the second spread position that can be created. In this second spread position, at the distal end of the haptic components 8, 9 and 10, a height H2 is attained that is twice the first height H1. In the first spread position, by contrast, a height of the first haptic element 5 in the direction of the principal optical axis A in the section plane is also greater than the first height H1 but less than the height H2 according to FIG. 4c.

In the non-spread state of the haptic element 5, the top side of the first haptic element 5 is disposed in a first position L1 in the space; cf. FIG. 4a. In the first spread position, this top side is displaced downward in the direction of the principal optical axis A and reaches a second position L2 in the space; cf. FIG. 4b. In the second spread position, an even greater compression force in the direction of the principal optical axis A is exerted by the second haptic component 9 on the first haptic component 8 and the third haptic component 10, such that the top side of the first haptic element 5 moves into a third position L3 even lower than position L2; cf. FIG. 4c.

FIG. 5 shows a top view of the first haptic element 5 of the intraocular lens 1 in a further embodiment. What is therefore shown is a diagram looking in the direction of the principal optical axis A. In this execution, it is apparent that cutouts 20 and 21 are provided in each case between the haptic components 8 to 10, such that they are not coherent along this extent of the cutouts 20 and 21. The haptic components 8 to 10 are thus bending bars that are displaceable at least in vertical direction at their respective distal ends 81, 91 and 101.

FIG. 5 shows two coupling depressions 18. These may also be formed in all other embodiments. It is thus possible for there to be corresponding coupling to an adjustment tool at different positions in radial direction. It is likewise possible here that an adjustment tool can mesh simultaneously into both coupling depressions, such that improved mechanical coupling is achieved here, and a corresponding adjusting movement is enabled. The spreading elements 14 and 17 are indicated here by dashed lines.

It may also be the case that the second spreading elements 15 to 16 extend up to the distal end 91 or end offset therefrom. It may be the case that the first spreading element 14 and 17 are formed up to the distal ends 81 and 101 or radially offset therefrom.

FIG. 6 shows a further working example of an intraocular lens 1 with a first haptic element 5. The diagram is viewed correspondingly to FIG. 5, such that the viewing direction here too is in the direction of the principal optical axis A onto the first haptic element 5. In this execution, the first haptic element 5 has a first haptic component 8, a second haptic component 10, and a land 83 that connects these two haptic elements 8 and 10. In addition, the first haptic element 5 also has, in the middle region, a second haptic component 9 spaced apart by cutouts 20, 21 and 22 from the first haptic component 8, the land 83 and the third haptic component 10, which form a frame around the second haptic component 9. In this execution, viewed in the plane at right angles to the principal optical axis A, the second haptic component 9 again takes the form of a radially extending bar or of a radially extending plate. More particularly, the first haptic component 8 together with the third haptic component 10 and the land 83 projects further radially outward than the second haptic component 9. The options for the configuration of the intraocular lens 1 that are elucidated for the examples according to FIGS. 2a to 5 may also be provided in the execution according to FIG. 6, apart from the fact that the spreading elements 14 to 17 cannot extend up to the distal ends 81 and 101.

It should be mentioned at this early stage that there are also possible additional or alternative working examples in which the spreading elements are formed so as to overlap in radial direction. More particularly, this may also be envisaged both in the non-spread position and in at least one possible spread position.

There are likewise possible working examples in which the spreading elements are formed so as to overlap both in azimuthal direction and in radial direction.

FIG. 7 shows a vertical section diagram through a working example of an intraocular lens 1 according to FIG. 5, in which the first haptic component 8 and the second haptic component 9 are in a non-spread position.

FIG. 8 shows a side view of the working example of the intraocular lens 1 according to FIG. 7, except that the second haptic component 9 is in a spread position relative to the first haptic component 8. The first haptic component 8 has a first edge line 84 present on the top side 85 at the distal end 81 of the first haptic component 8. In addition, the first haptic component 8 has a second edge line 86 present on the bottom side 87 at the distal end 81 of the first haptic component 8. Analogously, the second haptic component 9 has a third edge line 94 present on the top side 95 at the distal end 91 of the second haptic component 9. A fourth edge line 96 is formed on the bottom side 97 at the distal end 91 of the second haptic component 9. The first edge line 84 has an axial distance H3 from the fourth edge line 96, i.e. a distance H3 measured in the direction of the principal optical axis A.

This embodiment is particularly advantageous since it leads to a significant spread between the second haptic component 9 and the first haptic component 8, or the second haptic component 9 and the third haptic component 10. Between the third edge line 94 of the second haptic component 9 and the second edge line 86 of the first haptic component 8, a height H2 greater than twice the height H1 is attained.

FIG. 9 shows, in a cross section through a capsular bag 30, an intraocular lens 1 according to the embodiment shown in FIG. 8 with a first haptic component 8 and a second haptic component 9 of a first haptic element 5 and a second haptic element 6 respectively. It is apparent that a relatively high distance H4 between the optical body 2 and the capsular bag 30 is attainable.

FIG. 10 shows, in a cross section through a capsular bag, an intraocular lens 1 in a further embodiment. The first haptic component 8 here is executed so as to have relatively high flexural stiffness compared to the second haptic component 9. The second haptic component 9 with the second spreading element 15, in the case of displacement in the direction of the principal optical axis A, is thus bent distinctly downward, whereas the first haptic component 8 remains in its position virtually without sagging. This may already be sufficient to assure a sufficient distance H4 between the posterior wall of the capsular bag 30 and the reverse side 4 of the optical body 2, such that this region is flushed by chamber liquid and the formation of aftercataract can be reduced.

FIG. 11 shows a further embodiment of an intraocular lens 1 with a first haptic element 5 in a vertical section. The second haptic component 9 has a second spreading element 15 formed so as to be curved on the underside in a direction of extension that runs in a plane at right angles to the principal optical axis A. When the second haptic component 9 is moved upward in the direction of the principal optical axis A, the underside of the second spreading element 15 may come to rest flat on the top side of the first spreading element 14. The second spreading element 15 then exerts a compressive force directed downward onto this first haptic component 8 in an edge region of this first haptic component 8, which leads to sagging of the first haptic component 8; cf. FIG. 12. This is also applicable analogously to the further second spreading element 16, the curved underside of which touches the surface of the further first spreading element 17 in a two-dimensional manner. This results in a height H2 that reaches almost twice the magnitude of height H1 between the third edge line 94 of the second haptic component 9 and the second edge line 86 of the first haptic component 8. This embodiment is advantageous since the large areal contact between the second spreading element 15 and the top side 85 of the first haptic component 8 achieves a very stable spread connection 13.

FIG. 13 shows, in a schematic diagram, a further working example of an intraocular lens with a first haptic element 5 in a top view. In this embodiment, at least a second spreading element 15 and a further second spreading element 16 are provided. The second spreading elements 15 and 16 are in one-piece form with the second haptic component 9. In this working example, the first spreading elements 14 and 17 are formed by the haptic components 8 and 10. In the non-spread position shown in FIG. 13, the second spreading elements 15 and 16 are shown in a prestressed position. In this position, they are in an internal arrangement in cutouts 23 and 24 provided in side walls of the second haptic component 9, which face the haptic components 8 and 10. This prestressed position is maintained in that the second spreading elements 15 and 16 directly adjoin the haptic components 8 and 10. If the second haptic component 9 is then moved, especially moved around the bending line 11 relative to the other haptic components 8 and 10 in the direction of the principal optical axis A, vertically upward in this case, a position is attained during this movement in which the second spreading elements 15 and 16 are no longer positioned in contact with the facing side walls of the haptic components 8 and 10. In this position, the second spreading elements 15 and 16 pivot laterally upward and then adjoin the first spreading elements 14 and 17 on the top sides of the haptic components 8 and 10 for securing of the spread position formed. In this execution, it is only in the spread position that an overlap is formed between the first spreading elements 14 and 15 and the second spreading elements 16 and 17. The spread position is shown in schematic form in FIG. 14, in which a top view of the first haptic element 5 is shown.

The first haptic element 5 is manufactured as shown in FIG. 14, i.e. with a second spreading element 15 and further second spreading element 16 protruding laterally from the second haptic component 9. Before insertion of the intraocular lens 1 into an eye, the second spreading element 15 is pivoted by −90°, and the further second spreading element 16 is pivoted by +90°, such that the two spreading elements 15, 16 each mesh into the corresponding cutouts 23, 24, where they remain in a prestressed position. The intraocular lens is then implanted with the spreading elements 15, 16 in the prestressed position. When the intraocular lens 1 is present within the capsular bag, an operator displaces the second haptic component 9 in the direction of the principal optical axis A, and enables pivoting of the second spreading elements 15 and 16, so as to attain a spread position.

FIG. 15 shows a schematic top view of a further working example of an intraocular lens 1 with a first haptic element 5. This is preferably shown in accordance with the execution in FIG. 6, in which the first haptic component 8 is connected by means of a land 83 to the third haptic component 10 in the manner of a frame. The assembly composed of first haptic component 8, land 83 and third haptic component 10 has relatively high flexural stiffness. The land 83 is considered to form part of the first haptic component 8. The first haptic component 8 has a first spreading element 14, and the second haptic component 9 has a second spreading element 15; cf. FIG. 16a. The second spreading element 15 is disposed at a distal end 91 of the second haptic component 9 and forms an extension of this distal end 91, with the distal end 91 preferably having an end face 92 in a vertical arrangement. The course of the second spreading element 15 is preferably inclined relative to the end face 92 in cross section. The first haptic component 8 has a proximal end 82 which is in a complementary arrangement with and at a short distance from the distal end 91 with the second spreading element 15.

All components of the intraocular lens 1 are formed from a material having a Shore A hardness in the range from 60 to 100 according to ISO 7619-1; the components are thus relatively soft and elastically deformable. This is applicable to all embodiments disclosed in this document.

If the second haptic component 9 is displaced upward in the direction of the principal optical axis A, the second spreading element 15 abuts the land 83. On account of the low hardness of the second haptic component 9, it is radially compressed and can be displaced via the land 83 until the second spreading element 15 comes to rest against the first spreading element 14; see FIG. 16b.

This embodiment is advantageous since the haptic element 5 in this spread position reaches a height H2 which is more than twice the height H1.

REFERENCE SYMBOLS

1 Intraocular lens
2 Optical body

3 Front side of the optical body
4 Reverse side of the optical body
5 First haptic element
6 Second haptic element
7 Third haptic element
8 First haptic component
9 Second haptic component
10 Third haptic component
11 Bending line
12 Edge of the optical body
13 Spread connection
14 First spreading element
15 Second spreading element
16 Further second spreading element
17 Further first spreading element
18 Coupling depression
19 Position
20 Cutout
21 Cutout
22 Cutout
23 Cutout
24 Cutout
30 Capsular bag
81 Distal end of the first haptic component
82 Proximal end of the first haptic component
83 Land
84 First edge line
85 Top side of the first haptic component
86 Second edge line
87 Bottom side of the first haptic component
91 Distal end of the second haptic component
92 End face of the second haptic component
94 Third edge line
95 Top side of the second haptic component
96 Fourth edge line
97 Bottom side of the second haptic component
101 Distal end of the third haptic component
A Principal optical axis
E1 Plane of the first haptic element in non-spread position
H1 First height
H2 Second height
H3 Distance
H4 Distance
HL Center thickness
L1 First layer
L2 Second layer
L3 Third layer
M Geometric center

The invention claimed is:

1. An intraocular lens having an optical body and having a haptic element coupled to the optical body, wherein the haptic element has a first haptic component and a second haptic component formed adjacent thereto, which is movable elastically relative to the first haptic component, and having a principal optical axis that penetrates through a front side and a reverse side of the optical body, wherein the haptic element, measured in the direction of the principal optical axis, has a maximum of a first height, wherein the second haptic component is displaceable relative to the first haptic component from a non-spread position to a spread position in such a way that the haptic element, measured in the direction of the principal optical axis, attains a maximum of a second height which is greater than the first height, and, in the spread position, the second haptic component can be locked in place relative to the first haptic component, wherein the first haptic component has a first spreading element, and the second haptic component has a second spreading element, wherein the first spreading element and the second spreading element, viewed in a circumferential direction around the principal optical axis, at least in the spread position, are in a mutually overlapping arrangement and directly adjacent to one another at least in some regions.

2. The intraocular lens as claimed in claim 1, wherein the first spreading element and the second spreading element, at least in the spread position, are arranged so as to overlap one another in a radial direction proceeding from the principal optical axis and directly adjacent to one another at least in some regions.

3. The intraocular lens as claimed in claim 1, wherein the first spreading element and the second spreading element are respectively arranged on the first haptic component and the second haptic component such that, in the non-spread position of the first haptic component and the second haptic component, the first spreading element and the second spreading element do not protrude beyond the first haptic component and the second haptic component either in the direction of the principal optical axis or in the circumferential direction around the principal optical axis.

4. The intraocular lens as claimed in claim 1, wherein the first spreading element and the second spreading element are of wedge-shaped cross section.

5. The intraocular lens as claimed in claim 1, wherein the second height is greater than a center thickness of the optical body.

6. The intraocular lens as claimed in claim 1, wherein a coupling elevation or coupling depression formed on a top face of the second haptic component is set up for engagement of an adjustment tool for establishment of a specific spread position of the first haptic component and the second haptic component relative to one another.

7. The intraocular lens as claimed in claim 1, wherein the intraocular lens is a posterior chamber lens for implantation into a capsular bag of an eye.

8. The intraocular lens as claimed in claim 2, wherein the first spreading element and the second spreading element are arranged on the first haptic component and the second haptic component such that, in the non-spread position of the first haptic component and the second haptic component, the first spreading element and the second spreading element do not protrude beyond the first haptic component and the second haptic component either in the direction of the principal optical axis or in the circumferential direction around the principal optical axis.

9. The intraocular lens as claimed in claim 2, wherein the first spreading element and the second spreading element are of wedge-shaped cross section.

10. The intraocular lens as claimed in claim 3, wherein the first spreading element and the second spreading element are of wedge-shaped cross section.

11. The intraocular lens as claimed in claim 2, wherein the second height is greater than a center thickness of the optical body.

12. The intraocular lens as claimed in claim 3, wherein the second height is greater than a center thickness of the optical body.

13. The intraocular lens as claimed in claim 4, wherein the second height is greater than a center thickness of the optical body.

14. The intraocular lens as claimed in claim 2, wherein a coupling elevation or coupling depression formed on a top face of the second haptic component is set up for engagement of an adjustment tool for establishment of a specific spread position of the first haptic component and the second haptic component relative to one another.

15. The intraocular lens as claimed in claim 3, wherein a coupling elevation or coupling depression formed on a top face of the second haptic component is set up for engagement of an adjustment tool for establishment of a specific spread position of the first haptic component and the second haptic component relative to one another.

16. The intraocular lens as claimed in claim 4, wherein a coupling elevation or coupling depression formed on a top face of the second haptic component is set up for engagement of an adjustment tool for establishment of a specific spread position of the first haptic component and the second haptic component relative to one another.

17. The intraocular lens as claimed in claim 5, wherein a coupling elevation or coupling depression formed on a top face of the second haptic component is set up for engagement of an adjustment tool for establishment of a specific spread position of the first haptic component and the second haptic component relative to one another.

18. The intraocular lens as claimed in claim 2, wherein the intraocular lens is a posterior chamber lens for implantation into a capsular bag of an eye.

19. The intraocular lens as claimed in claim 3, wherein the intraocular lens is a posterior chamber lens for implantation into a capsular bag of an eye.

20. The intraocular lens as claimed in claim 4, wherein the intraocular lens is a posterior chamber lens for implantation into a capsular bag of an eye.

* * * * *